(12) United States Patent
Neumeyer et al.

(10) Patent No.: US 6,844,438 B2
(45) Date of Patent: Jan. 18, 2005

(54) N-SUBSTITUTED DERIVATIVES OF MORPHINAN AND USES THEREOF

(75) Inventors: John L. Neumeyer, Wayland, MA (US); Jean M. Bidlack, Rochester, NY (US); Xiao-Hui Gu, San Diego, CA (US)

(73) Assignees: McLean Hospital Corporation, Belmont, MA (US); University of Rochester, Rochester, NY (US)

( * ) Notice: Subject to any disclaimer, the term of this patent is extended or adjusted under 35 U.S.C. 154(b) by 0 days.

(21) Appl. No.: 10/222,736

(22) Filed: Aug. 15, 2002

(65) Prior Publication Data

US 2003/0073716 A1 Apr. 17, 2003

Related U.S. Application Data

(60) Provisional application No. 60/312,682, filed on Aug. 15, 2001.

(51) Int. Cl.[7] .................. A61K 31/485; A61K 51/00; C07D 221/28
(52) U.S. Cl. .................. 546/74; 424/9.44; 514/289; 546/4
(58) Field of Search .................. 546/74; 424/9.44; 514/289

(56) References Cited

U.S. PATENT DOCUMENTS

| 3,767,658 | A | * | 10/1973 | Atsumi et al. | |
|---|---|---|---|---|---|
| 3,917,606 | A | * | 11/1975 | Merz et al. | |
| 4,767,718 | A | | 8/1988 | Meyers | 436/501 |
| 4,806,341 | A | | 2/1989 | Chien et al. | 424/448 |
| 4,992,445 | A | | 2/1991 | Lawter et al. | 514/279 |
| 5,506,359 | A | | 4/1996 | Madras et al. | 546/130 |
| 5,770,180 | A | | 6/1998 | Madras et al. | 424/1.81 |
| 6,004,962 | A | | 12/1999 | Gooberman | 514/255 |
| 6,156,769 | A | | 12/2000 | Farrar et al. | 514/320 |
| 6,174,891 | B1 | | 1/2001 | Nagase et al. | 514/282 |

FOREIGN PATENT DOCUMENTS

| WO | WO 94/04146 | 3/1994 | A61K/31/35 |
|---|---|---|---|
| WO | WO 97/40859 | 11/1997 | A61K/51/04 |

OTHER PUBLICATIONS

"Apomorphine New Uses for an Old Drug" Neumeyer and Baldessari, et al., Pharmaceutical News, vol. 4, No. 6, pp. 12–16, 1997.

"Dopamine Transporter Imaging with Florine–18–FPCIT and PET" Kazumata, et al., The Journal of Nuclear Medicine, vol. 39, No. 9, pp. 1551–1530, Sep. 1998.

"Kappa Opioid Agonists as Targets for Pharmacotherapies in Cocaine Abuse" Neumeyer, et al., Pharmaceutica Acta Helvetiae 74, pp. 337–344, 2000.

"Synthesis and Opioid Receptor Affinity of Morphinan and Benzomorphan Derivatives: Mixed κ Agonists and μ Agonists/Antagonists as Potential Pharmacotherapeutics for Cocaine Dependence" Neumeyer, et al., Journal of Medicinal Chemistry, vol. 43, No. 1, pp. 114–122, 2000.

* cited by examiner

Primary Examiner—Bernard Dentz
(74) Attorney, Agent, or Firm—Fish & Richardson P.C.

(57) ABSTRACT

The invention is based in part on the discovery that nonselective κ agonists that possess μ receptor-mediated effects in addition to their κ agonist effects can decrease cocaine self-administration more effectively and with fewer undesirable side effects than can highly selective κ agonists. The invention includes a number of new compounds having both nonselective κ opioid receptor agonist activity and additional activity at μ opioid receptors. These compounds are useful for the treatment of cocaine abuse, and can also be radiolabeled for use as imaging agents, e.g., the N-fluoroalkyl and iodoalkyl derivatives can be used, respectively, for positron emission tomography (PET) and single photon computed tomography (SPECT) brain imaging.

25 Claims, 6 Drawing Sheets

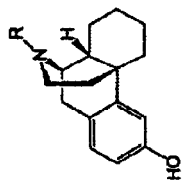

| | compound | R | molecular formula | yield (%) | mp (°C) | anal.[a] |
|---|---|---|---|---|---|---|
| 3 | MCL-107 | | $C_{19}H_{26}NOF$ | 83 | 215-216[b] | C, H, N |
| 4 | MCL-108 | | $C_{20}H_{29}NO·0.25H_2O$ | 62 | 164-165[c] | C, H, N |
| 5 | MCL-109 | | $C_{20}H_{29}NO_2·0.5H_2O$ | 69 | 164-166 | C, H, N |
| 6 | MCL-110 | | $C_{19}H_{27}NO_2·0.75H_2O$ | 95 | 181-183 | C, H, N |
| 7 | MCL-111 | | $C_{23}H_{27}NO·0.25H_2O$ | 95 | 165-167 | C, H, N |
| 8 | MCL-113 | | $C_{19}H_{59}NO·0.25H_2O$ | 61 | 172-174 | C, H, N |
| 9 | MCL-117 | | $C_{19}H_{23}NO$ | 55 | 203-204 (dec) | C, H, N |
| 10 | MCL-124 | | $C_{19}H_{24}F_3NO$ | 45 | foam | C, H, N |
| 11 | MCL-125 | | $C_{19}H_{24}N_2O·0.45H_2O$ | 61 | foam[d] | C, H, N |
| 12 | MCL-126 | | $C_{20}H_{26}N_2O·0.25H_2O$ | 75 | 158-160 | C, H, N |
| 13 | MCL-127 | | $C_{24}H_{29}NO·0.25H_2O$ | 56 | 130-132 | C, H, N |
| 20 | MCL-104 | | $C_{22}H_{31}NO$ | 68 | 229-230[e] | C, H, N |
| 21 | MCL-105 | | $C_{23}H_{33}NO$ | 73 | 242-243[c] | C, H, N |
| 22 | MCL-119 | | $C_{29}H_{33}NO_2·0.75H_2O$ | 33 | 105-110[e] | C, H, N |
| 23 | MCL-120 | | $C_{21}H_{25}NOS·0.25H_2O$ | 38 | 218-220 | C, H, N |
| 24 | MCL-112 | | $C_{24}H_{29}NO·0.25H_2O$ | 39 | 233-235 | C, H, N |
| 26 | MCL-114 | | $C_{25}H_{29}NO_2·0.25H_2O$ | 82 | foam | C, H, N |
| 27 | MCL-115 | | $C_{25}H_{29}NO_2$ | 76 | 166-168 (dec) | C, H, N |

FIG. 1A

| | | | | | |
|---|---|---|---|---|---|
| 28 | MCL-123 | ![structure] | $C_{23}H_{27}NO_3 \cdot 1.25H_2O$ | 74 | foam | C, H, N |
| 29 | MCL-122 | ![structure] | $C_{23}H_{29}NO_2S \cdot 1.75H_2O$ | 64 | foam | C, H, N |
| 30 | MCL-121 | ![structure] | $C_{25}H_{31}NO_2 \cdot 0.5H_2O$ | 79 | 218-220 (dec) | C, H, N |
| 31 | MCL-128 | ![structure] | $C_{23}H_{29}NO_3$ | 51 | foam | C, H, N |
| 34 | MCL-118 | ![structure] | $C_{19}H_{24}INO \cdot 0.25H_2O$ | 32 | 165-167 (dec) | C, H, N |
| 35 | MCL-116 | | $C_{19}H_{24}INO \cdot 0.25H_2O$ | 15 | 210-214 (dec) | C, H, N |

*The C, H, N analyses are within ± 0.4% of theoretical values. *L*-tartrate salt recrystallized from MeOH. *Recrystallized from EtOAc. *Jacobson et al.³⁸ reported that the free base is an oil and the mp of its HCl salt was 188 °C (softening at 160 °C). *(S)-mandelate salt recrystallized from MeOH-'PrOH.

FIG. 1B

*Reagents and conditions:* (a). ethyl chloroformate, K₂CO₃, CHCl₃, reflux; 10% NaOH, MeOH; glacial HOAc, HCl (12 N), reflux; (b). RBr, K₂CO₃ or NaHCO₃, DMF, rt or 90 °C; (c). RCOCl, Et₃N, CH₂Cl₂, 0 °C–rt; (d). LiAlH₄, THF, rt; (e). ArCOCH₂CH₂NMe₃I, DMF, Na₂CO₃, rt; (f). NaBH₄, MeOH, rt.

Reagents and conditions: (a). Bu₃SnH, Et₃B, THF; column separation; (b). I₂, CHCl₃.

| Compound | K$_i$ (nM) ± SEM | | | Selectivity | |
|---|---|---|---|---|---|
| | [$^3$H]DAMGO (μ) | [$^3$H]Naltrindole (δ) | [$^3$H]U69,593 (κ) | κ/μ | κ/δ |
| U 50,488 | 220±5.6 | 2500±170 | 0.36±0.056 | 610 | 6900 |
| Mr2033 | 0.40±0.07 | 4.5±0.70 | 0.21±0.044 | 2 | 20 |
| (-)EKC | 0.78±0.10 | 3.4±0.41 | 0.62±0.11 | 1 | 5 |
| Levorphanol | 0.21±0.017 | 4.2±2.3 | 2.3±0.26 | 0.09 | 2 |
| (-) Cyclorphan | 0.092±0.005 | 0.22±0.01 | 0.053±0.003 | 2 | 4 |
| MCL-101 | 0.12±0.012 | 1.3±0.06 | 0.073±0.012 | 2 | 18 |
| 20 (MCL-104) | 0.96±0.13 | 6.9±0.68 | 0.21±0.014 | 5 | 33 |
| 21 (MCL-105) | 18±1.3 | 69±5.3 | 1.5±0.19 | 12 | 46 |
| 3 (MCL-107) | 0.18±0.025 | 0.85±0.021 | 0.083±0.002 | 2 | 10 |
| 4 (MCL-108) | 0.54±0.15 | 5.6±0.70 | 0.16±0.25 | 3 | 35 |
| 5 (MCL-109) | 0.26±0.02 | 5.6±0.040 | 0.33±0.015 | 0.8 | 16 |
| 6 (MCL-110) | 0.11±0.007 | 0.54±0.05 | 0.094±0.001 | 1 | 6 |
| 7 (MCL-111) | 20±2.9 | 420±77 | 1.9±0.19 | 11 | 220 |
| 24 (MCL-112) | 0.12±0.015 | 3.1±0.88 | 1.3±0.26 | 0.092 | 2 |
| 8 (MCL-113) | 0.34±0.008 | 4.1±0.50 | 0.16±0.031 | 2 | 26 |
| 26 (MCL-114) | 0.27±0.035 | 10.0±2.1 | 4.5±0.82 | 0.06 | 2 |
| 27 (MCL-115) | 0.43±0.11 | 23±2.6 | 9.9±1.2 | 0.04 | 2 |
| 35 (MCL-116) | 0.42±0.15 | 33±6.2 | 0.65±0.06 | 0.6 | 51 |
| 9 (MCL-117) | 0.0032±0.001 | 0.62±0.19 | 0.0030±0.0005 | 1 | 210 |
| 34 (MCL-118) | 0.0048±0.001 | 27±4.9 | 0.037±0.007 | 0.13 | 730 |
| 22 (MCL-119) | 0.54±0.04 | 8.5±1.1 | 0.13±0.004 | 4 | 65 |
| 23 (MCL-120) | 1.5±0.16 | 51±6.3 | 0.32±0.015 | 5 | 160 |
| 30 (MCL-121) | 21±8.8 | 130±16 | 57±2.1 | 0.4 | 2 |
| 29 (MCL-122) | 4.1±0.27 | 110±9.5 | 25±0.62 | 0.2 | 4 |
| 28 (MCL-123) | 0.28±0.06 | 42±5.4 | 7.9±0.26 | 0.035 | 5 |
| 10 (MCL-124) | 2.3±0.44 | 27±1.7 | 1.3±0.10 | 2 | 21 |
| 11 (MCL-125) | 0.33±0.01 | 2.6±0.95 | 0.23±0.05 | 1.4 | 11 |
| 12 (MCL-126) | 0.16±0.02 | 3.1±0.38 | 0.38±0.008 | 0.42 | 8 |
| 13 (MCL-127) | 0.92±0.29 | 33±1.6 | 15±3.6 | 0.06 | 2 |
| 31 (MCL-128) | 4.2±0.36 | 29±2.4 | 12±1.9 | 0.35 | 2 |

FIG. 4

N-SUBSTITUTED DERIVATIVES OF MORPHINAN AND USES THEREOF

CROSS REFERENCE TO RELATED APPLICATION

This application claims priority from Provisional Application 60/312,682 filed Aug. 15, 2001.

STATEMENT AS TO FEDERALLY SPONSORED RESEARCH

This invention was made with Government support under grant numbers K05-DA00360, U-19-DA11007, and K05-DA00101, awarded by National Institute on Drug Abuse. The Government has certain rights in the invention.

FIELD OF THE INVENTION

This invention relates to N-substituted morphinan compounds and uses thereof.

BACKGROUND OF THE INVENTION

The abuse of cocaine and other stimulant drugs is a significant social and public health concern throughout the world (Crome, *Drug Alcohol Dependence*, 55:247, 1999). Drug abuse has contributed greatly to the increasing spread of HIV and HBV (Sorensen et al., *Drug Alcohol Dependence*, 59:17, 2000). Currently there are no efficacious medications for the treatment of cocaine abuse (Mendelson et al., *N. Engl. J. Med.*, 334:965, 1996; Carroll et al., *J. Med. Chem.*, 42:2721, 1999).

Although the mesolimbic dopamine pathway is believed to play a primary role in mediating the locomotor, discriminative stimulus, and reinforcing effects of cocaine (Smith et al., *Drug Discovery Today*, 2:322, 1999; Wingler, in "Cocaine Abuse: Behavior, Pharmacology and Clinical Application," Higgens, S. T., Katz, J. L., Eds., Academic: San Diego, 1998, pp. 135–158, 1998; Kuhar et al., *Trends Neurosci.*, 14:299, 1991; Ritz et al., *Science*, 237:1219, 1987), other neurotransmitter systems have also been implicated in the reinforcing effect of cocaine (Walsh et al., *Psychopharmacology*, 130:41, 1997; Rocha et al., *Nature: Neuroscience*, 1:132, 1998; Giros et al., *Nature*, 379:606, 1996; Rocha et al., *Nature*, 393:175, 1998; Witkin et al., *Life Sci.*, 53:PL405, 1993; Dewey et al., *Synapse*, 30:119, 1998; Negus et al., *Psychopharmacology*, 152:398, 2000).

There is increasing evidence that opioid receptor agonists modulate the neurochemical and behavioral effects of cocaine. For example, kappa (κ) receptor agonists attenuate cocaine-induced increases in dopamine levels in the nucleus accumbens (Maisonneuve et al., *Neurosci. Lett.*, 181:57, 1994; Heidbreder et al., *NeuroReport*, 5:1797, 1994). Administration of κ opioid receptor agonists has also been reported to attenuate the discriminative stimulus properties (Spealman et al., *J. Pharmacol. Exp. Ther.*, 26:607, 1992; Spealman et al., *Behav. Pharmacol.*, 5:21, 1994; Riberdy et al., *Soc. Neurosci. Abstr.*, 21:718, 1995), conditioned reinforcing effects (Shippenberg et al., *J. Pharmacol. Exp. Ther.*, 276:545, 1996; Shippenberg et al., *Eur. J. Pharmacol.*, 345:27, 1998; Crawford et al., *Psychopharmacology*, 120:392, 1995), and self-administration of cocaine (Glick et al., *Brain Res.*, 681:147, 1995; Mello et al., *J. Pharmacol. Exp. Ther.*, 286:812, 1998; Schenk et al., *Psychopharmacology*, 144:339, 1999; Negus et al., *J. Pharmacol. Exp. Ther.*, 282:44, 1997; Kuzmin et al., *Eur. J. Pharmacol.*, 321:265, 1997). Further, κ opioid agonists have been reported to attenuate the reinstatement of extinguished drug-taking behavior in an animal model of relapse (Schenk et al., *Psychopharmacology*, 144:339, 1999; Schenk et al., *Psychopharmacology*, 151:85, 2000). Taken together, these findings suggest that activation of κ opioid receptors may functionally antagonize some abuse-related effects of cocaine, possibly by inhibiting the release of dopamine from dopaminergic neurons, and thus offers a novel and effective pharmacological approach to treat cocaine abuse.

SUMMARY OF THE INVENTION

The invention is based, in part, on the discovery that nonselective κ agonists that induce μ receptor-mediated effects in addition to their κ agonist effects can decrease cocaine self-administration more effectively and with fewer undesirable side effects than can highly selective κ agonists. The invention includes a number of new morphinan-3-ol compounds having both nonselective κ opioid receptor agonist activity and additional activity at μ opioid receptors. The new compounds have relatively low affinity for the δ opioid receptor, and, thus, do not interact significantly with the δ receptor or produce side effects associated with activity at the δ receptor. These compounds are useful for the treatment of cocaine abuse, and can also be radiolabeled for use as imaging agents (e.g., the N-fluoroalkyl and iodoalkyl derivatives can be used, respectively, for positron emission tomography (PET) and single photon computed tomography (SPECT) brain imaging).

In general, the invention features compounds of formula I for use in various new methods described herein:

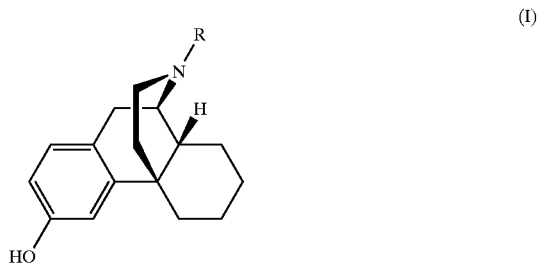

(I)

where R can be fluoropropyl (i.e., the compound can be compound 3 of FIGS. 1A and 1B), isopropyl (compound 4), 2-ethoxyethyl (compound 5), 2-methoxyethyl (compound 6), propargyl (compound 9), 3,3,3-trifluoropropyl (compound 10), 3-cyanopropyl (compound 12), cyclopentylmethyl (20), furanylmethyl (22), thienylmethyl (23), 3-iodoprop-(2E)-enyl (34), or 3-iodoprop-(2Z)-enyl (35), or a salt thereof. The compound can alternatively be any one of compounds 3, 5, 6, 10, 12, 23, 26–31, 34, or 35 of FIGS. 1A and 1B, or a salt thereof.

In another embodiment, the invention features a single-photon computed tomography (SPECT) imaging reagent. The reagent can be labeled with a radioactive label, e.g., iodine, such as either $^{123}$I-labelled compound 34 or $^{123}$I-labeled compound 35 (as shown in FIGS. 1A and 1B). Other compounds of FIGS. 1A and 1B can also be labeled and used to prepare such a reagent. The invention also features a method of SPECT imaging of brain opioid receptors (such as kappa opioid receptors). The method includes obtaining a new compound described herein, and labeling it with an appropriate label, e.g., an $^{123}$I-labeled compound of FIGS. 1A and 1B, such as compounds 34 or 35, administering the labeled compound to a patient (e.g., by injection); and obtaining brain scans with a SPECT camera to image, e.g., localize and/or quantify, the receptors.

In another embodiment, the invention features a positron emission tomography (PET) imaging reagent. The reagent can be labeled with a radioactive label, e.g., fluorine, such as an $^{18}$F-labeled compound 3 or 10 (as shown in FIGS. 1A and 1B), or compound 1. Other reagents can be made from other compounds in FIGS. 1A and 1B labeled in the same way. The invention also features a method of PET imaging of brain opioid receptors (such as kappa opioid receptors). The method includes obtaining one of the new compounds and labeling the compound to create, e.g., an $^{18}$F-labeled compound of FIGS. 1A and 1B, such as compounds 3 or 10 as referenced herein, administering the labeled compound to a patient (e.g., by injection); and obtaining brain scans with a PET camera to image, e.g., localize and/or quantify said receptors.

In still another embodiment, the invention features a method of treating a patient addicted to cocaine. The method includes the steps of administering to the patient an effective amount of a compound of formula I; where R can be, for example, hydrogen (—H), alkyl, cycloalkyl, alkenyl, alkynyl, aryl, aralkyl, alkoxy, aryloxy, arylcarbonyl, cyanoalkyl, aminoalkyl, haloalkyl, haloalkenyl, α-hydroxyaralkyl, or other substituted alkyl group; or a 10-ketomorphinan analog thereof. For example, the compound can be any one or more of compounds 3, 4, 5, 6, 8, 9, 11, 12, 34, or 35.

In still another embodiment, the invention features a method of identifying a drug useful for treating a patient addicted to cocaine. The method includes identifying a compound having nonselective κ opioid receptor agonist activity and either μ opioid receptor agonist or antagonist activity. The invention also features a method of making a pharmaceutical formulation by identifying a drug using the new methods, and then mixing the drug with a physiologically acceptable excipient to prepare the formulation. The invention also features a method of treating a patient addicted to cocaine, by administering to the patient an effective amount of the drug, or the pharmaceutical formulation including the drug, identified by the above method.

As used herein, the term "agonist" refers to compounds that produce a physiological effect mediated by a receptor.

As used herein, the term "antagonist" refers to compounds that bind to the same receptors as do corresponding agonists, but do not produce the physiological effect produced by the agonist. By binding to the receptor, the antagonist can, for example, inhibit the binding of an agonist to the same receptor. Thus, the presence of the antagonist can prevent the production of the physiological effect even though the agonist is also present.

The "nonspecific" agonists of the invention bind with high affinity to more than one type of opioid receptor, specifically, both κ and μ.

The terms "bonded," "binding," "binds," or "bound," as used herein, can refer to, for example, covalent, ionic, van der Waals, or hydrophobic interactions. Coordination complexes and hydrogen bonding are also contemplated. Typically, the bonding interactions are reversible, but can be irreversible in some cases.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention provides several advantages. For example, κ agonists with varying degrees of activity have fewer side effects than do κ-selective compounds. Activity at the μ receptor appears to decrease side effects such as sedation and dysphoria.

Because certain of the new compounds contain a group that can be radiolabeled, these compounds can be administered in very low quantities to humans for use in tomographic imaging of the brain, allowing the binding of the compounds to different brain regions to be monitored. An advantage of using these compounds for PET and SPECT imaging is that they can enable determination of the localization and density of κ opioid receptors in human brain tissue. The new compounds can also be useful to determine if the amount of κ opioid receptor in brain changes as a result of cocaine use.

Other features and advantages of the invention will be apparent from the following detailed description, and from the claims.

BRIEF DESCRIPTION OF DRAWINGS

FIGS. 1A and 1B together form a table of various N-substituted morphinans and their physical properties.

FIG. 4 is a table of binding affinities of the compounds of FIG. 1 for the μ, δ, and κ opioid receptors.

DETAILED DESCRIPTION OF THE INVENTION

A series of new N-substituted derivatives of morphinan were synthesized, and their binding affinity for three opioid receptors (i.e., μ, δ, and κ) was determined. A paradoxical effect of N-propargyl (MCL-117) and N-(3-iodoprop-(2E)-enyl) (MCL-118) substituents on the binding affinities for the μ and κ opioid receptors was observed. All of these novel derivatives showed a preference for the μ and κ versus δ binding.

To systematically study the effects of N-substituents in the morphinan nucleus on binding affinity, selectivity, and efficacy at μ and κ opioid receptors, a variety of substituents were introduced on the nitrogen atom in morphinan, and then the new derivatives were assayed for biological activity. The κ/δ selectivity of most of these derivatives was considerably better than that of levorphanol and ethylketocyclazocine (EKC).

Chemical Synthesis

Figure 2:
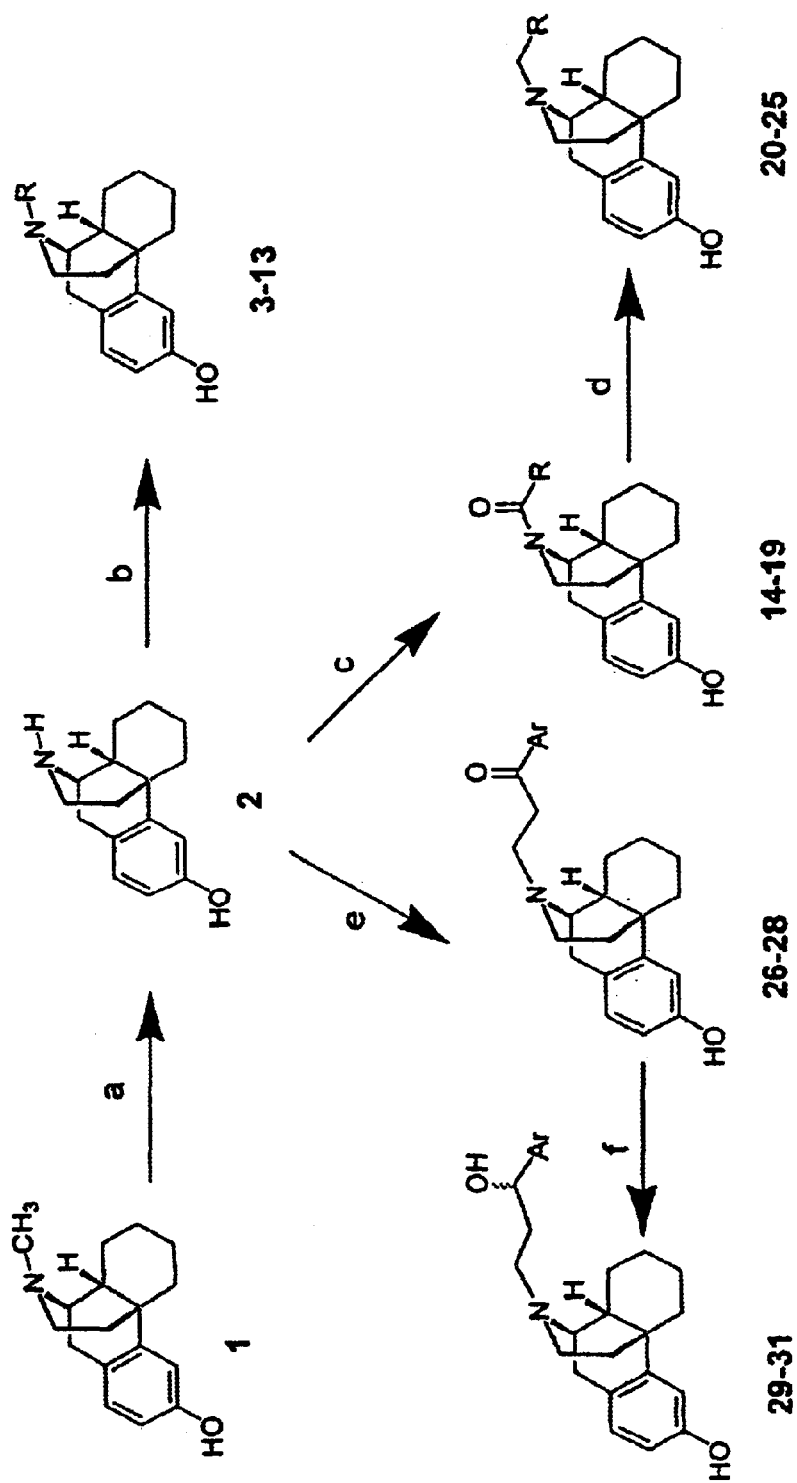
FIG. 2 is a reaction scheme illustrating three methods for the synthesis of N-substituted morphinans.

The target derivatives 3–13 and 20–31, shown in FIG. 1 were synthesized from norlevorphanol 2 by one of the three methods as depicted in FIG. 2. Demethylation of levorphanol 1 was accomplished according to the procedure reported by DeGraw and Engstrom (*J. Labelled Compd.* 11:233, 1975). Thus, levorphanol was treated with ethyl chloroformate in refluxing chloroform in the presence of $K_2CO_3$ followed by partial hydrolysis of the product with 10% NaOH in methanol. Norlevorphanol 2 was obtained in good yield after hydrolysis of the resulting carbamate (structure not shown) intermediate in a mixture of hydrochloric acid and glacial acetic acid. Direct alkylation of norlevorphanol with various alkyl halides in dimethyl formamide (DMF) using $K_2CO_3$ or $NaHCO_3$ as a base provided N-substituted derivatives 3–13 in good to excellent yields (all final compounds were characterized by NMR and mass spectroscopy, and gave satisfactory C, H, and N analyses, i.e., within +0.4% of theoretical values).

In an alternative procedure, acylation of norlevorphanol with acid chlorides followed by reduction of the intermediate amide 14–19 with $LiAlH_4$ in tetrahydrofuran (THF) afforded the tertiary amines 20–25.

Figure 3:
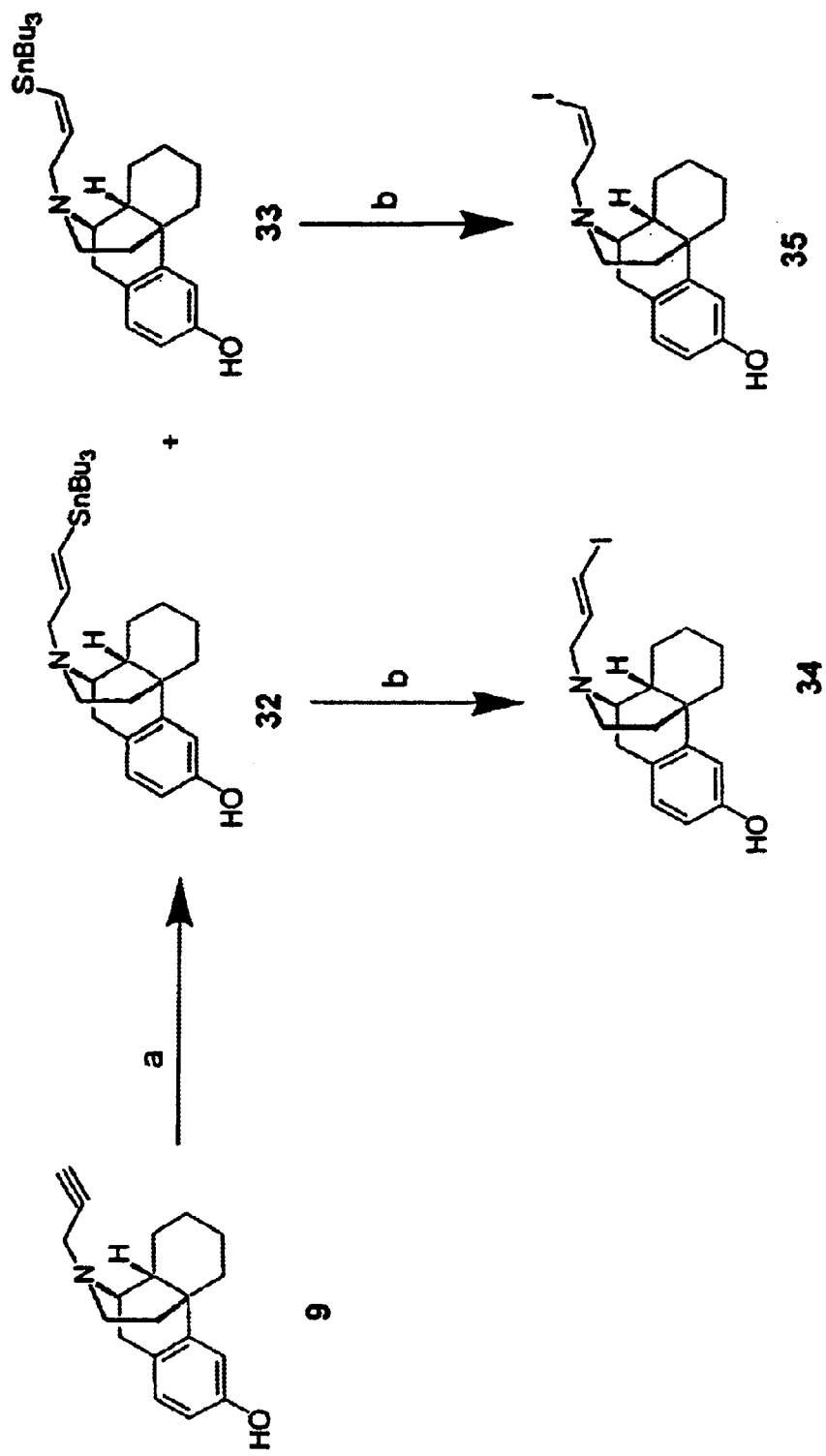
FIG. 3 is a reaction scheme illustrating the iododestannylation reaction used in the synthesis of N-(3-iodoprop-(2E)-enyl)morphinan 34 and N-(3-iodoprop-(2Z)-enyl) morphinan 35.

Alkylation of norlevorphanol with 1-aryl-3-(dimethylamino)-1-propanone methiodide in DMF in the presence of $Na_2CO_3$ yielded ketones 26–28, which were then reduced with $NaBH_4$ to afford the alcohols 29–31 as a mixture of hydroxy diastereomers. The N-(3-iodoprop-(2E)-enyl) and N-(3-iodoprop-(2Z)-enyl) derivatives 34 and 35 were obtained by iododestannylation of compounds 32 and 33 by treatment with iodine in chloroform. The reaction scheme is shown in FIG. 3. The tributyltin precursors 32 and 33 were prepared by hydrostannylation of the N-propargyl derivative 9 with $HSnBu_3$ in the presence of $Et_3B$ as catalyst followed by column separation of the two isomers (see Goodman et al., *J. Med. Chem.*, 37:1535, 1994). Another efficient route to the (E)-tributyltin precursor 32 involved alkylation of norlevorphanol with 3-(tributylstannyl)prop-(2E)-enyl chloride, which was prepared by chlorination of 3-(tributylstannyl)prop-(2E)-en-1-ol with $PPh_3$ and $CCl_4$. The (E)-stannyl alcohol was obtained by hydrostannylation of propargyl alcohol using the literature procedure of Emond et al., *J. Med. Chem.*, 40:1366 (1997). The structures and physical properties of these new N-substituted derivatives are shown in FIG. 1.

Assays for Binding Affinity

The binding affinities of compounds 3–13, 20–24, 26–31, 34, and 35 for the $\mu$, $\delta$, and $\kappa$ opioid receptors were assessed using competitive binding assays in guinea pig brain membranes employing [$^3$H]DAMGO ($\mu$ agonist), [$^3$H]naltrindole ($\delta$ antagonist) and [$^3$H]U69,593 ($\kappa$ agonist) as radioligands, using the methods described in Neumeyer et al., *J. Med. Chem.*, 43:114 (2000). The results are summarized in FIG. 4. For comparison purposes, the binding data for U50,488, Mr2033, EKC, levorphanol, and cyclorphan are also included in FIG. 4. Antinociceptive biological data can also be obtained using the tail-flick and/or mouse writhing tests (Id.).

Analysis of Data

The N-substituent has a significant effect on both the opioid receptor binding affinity and selectivity of these morphinan derivatives. For example, our previous research indicated that replacement of the methyl group in levorphanol with a cyclopropylmethyl group can greatly increase affinity at the $\delta$ and $\kappa$ opioid receptors (20-fold and 40-fold, respectively), while the affinity at the $\mu$ opioid receptor increases just 2-fold (Id.). The N-cyclobutylmethyl analog MCL-101 showed 30-fold increase in binding affinity at the $\kappa$ opioid receptor, but the increase for the $\mu$ and $\delta$ opioid receptors was less pronounced (2-fold and 3-fold, respectively). MCL-101 possessed almost the same affinity for the $\mu$ and $\kappa$ opioid receptors as cyclorphan, but MCL-101 had greater $\kappa/\delta$ selectivity (18-fold vs 4-fold). Further increasing the size of the ring led to a loss in binding affinity. Consistent with this observation, the N-cyclohexylmethyl derivative 21 (MCL-105) displays very low affinity for the three opioid receptors.

Surprisingly, the N-propargyl derivative 9 (MCL-117) and the N-(3-iodoprop-(2E)-enyl) derivative 34 (MCL-118) exhibited unexpectedly high affinity for the $\mu$ and $\kappa$ opioid receptors with $K_i$ values in the picomolar range. In fact, these two compounds are among the most potent ligands for the $\mu$ and $\kappa$ opioid receptors identified to date. Compounds 9 and 34 had the same high affinity for the $\mu$ opioid receptor, but 34 displayed 10-fold decreased affinity for the $\kappa$ and 43-fold decreased affinity for the $\delta$ opioid receptor in comparison to compound 9. The N-(3-iodoprop-(2Z)-enyl) derivative 35, however, displayed dramatically decreased (100-fold and 17-fold) affinity for the $\mu$ and $\kappa$ receptors relative to 34. The N-isopropyl derivative 4 (MCL-108) showed much higher (14-fold) affinity for the $\kappa$ receptor but lower (2-fold) affinity for the $\mu$ receptor than levorphanol. Replacement of the methyl with an allyl group 8 (MCL-113, levallorphan) resulted in 15-fold increase in affinity for the $\kappa$ opioid receptor and almost no changes in affinity for both of the $\delta$ and $\mu$ opioid receptors. The N-(3-fluoropropyl) derivative 3 (MCL-107) also displayed very high affinity for all three opioid receptors ($K_i$=0.18 nM, 0.85 nM, and 0.083 nM for the $\mu$, $\delta$, and $\kappa$ receptor, respectively).

The N-methoxyethyl derivative 6 (MCL-110) was found to have high affinity for the $\kappa$ and $\mu$ opioid receptors ($K_i$=0.094 nM and 0.11 nM, respectively). Replacement of methoxyethyl with ethoxyethyl resulted in a 2-fold and 4-fold loss in affinity for the $\mu$ and $\kappa$ opioid receptors, respectively. The N-phenoxyethyl derivative 13 (MCL-127) exhibited decreased affinity for all three opioid receptors relative to the methoxyethyl derivative 6.

Without intending to be bound by any theory, it appears that the size of the ether chain affects the affinity for the three opioid receptors. The N-methoxymethyl and N-fluoropropyl derivatives of normetazocine were found to bind nonselectively, with high affinity for the $\mu$ and $\kappa$ receptors. The N-furanylmethyl derivative 22 (MCL-119) displayed high affinity for the $\mu$ and $\kappa$ receptors ($K_i$=0.54 nM and 0.13 nM, respectively). Replacement of the furanylmethyl group with thienylmethyl resulted in decreased affinity for all three opioid receptors, but this decrease was most pronounced for the $\delta$ opioid receptor (6-fold vs. 2-fold). Thus, the N-thienylmethyl derivative 23 (MCL-120) displayed good selectivity for the $\mu$ and $\kappa$ receptors versus $\delta$ receptor ($\kappa/\delta$=160, $\mu/\delta$=14).

The N-benzyl derivative 7 (MCL-111) showed dramatically decreased affinity at all three opioid receptors relative to 22 and 23. Adding one more methylene unit between the nitrogen and the phenyl ring (i.e., the phenethyl derivative 24) led to a great increase in binding affinity. The increase is 130-fold and 16-fold for the $\delta$ and $\mu$ opioid receptors, respectively.

The N-cyanoethyl derivative 11 (MCL-125) displayed increased affinity (10-fold) for the $\kappa$ opioid receptor as compared with levorphanol (the N-methyl derivative). Replacement of the 2-cyanoethyl with a 3-cyanopropyl group caused few changes in binding affinity for all three opioid receptors. However, the N-trifluoropropyl derivative 12 had decreased affinity for the $\mu$ and $\delta$ receptors and similar affinity for the $\kappa$ receptor relative to levorphanol.

The three Mannich base derivatives 26–28 showed similar binding profiles with good affinity for the $\mu$ opioid receptor and low affinity for both the $\kappa$ and $\delta$ opioid receptors. Reduction of the keto group to secondary alcohol resulted in loss in binding affinity for the three opioid receptors. Again without wishing to be bound by any theories, it seems that a hydroxyl group in the N-substituent interferes with the interaction of the ligand with the opioid receptors, probably due to the hydroxyl group's hydrogen-donating property.

In conclusion, the N-substituent of morphinan had significant effect on the binding affinity and selectivity for the three opioid receptors. These N-substituted derivatives exhibited a strong preference for $\mu$ and $\kappa$ versus $\delta$ binding. The N-(3-fluoropropyl) 3 (MCL-107), N-methoxyethyl 6 (MCL-110), the N-propargyl 9 (MCL-117), and the N-(3-iodoprop-(2E)-enyl) 34 (MCL-118) derivatives possessed high affinity for the $\mu$ and $\kappa$ opioid receptors. In particular, the N-propargyl analogue 9 (MCL-117) and the N-(3-iodoprop-(2E)-enyl) analog 34 (MCL-118) showed very high affinity for the $\mu$ and $\kappa$ opioid receptors with $K_i$ values in the picomolar range. As noted above, the new compounds can be assayed for in vivo activity using, for example, the tail flick assay as described by Neumeyer et al. (J. Med. Chem., 43:114–122, 2000) and McLaughlin et al. (J. Pharmacol. Exp. Ther., 289:304–311, 1999), and/or the acetic acid writhing test described by Neumeyer et al. (J. Med. Chem., 43:114–122, 2000) and Xu et al. (J. Pharmacol. Exp. Ther., 279:539–547, 1996).

Preparation and Administration of Pharmaceutical Formulations

The new compounds for use in accordance with the present invention can be formulated in a conventional manner using one or more physiologically acceptable carriers or excipients.

Agents used in the formulations and their physiologically acceptable salts and solvates can be prepared for administration by various methods. For example, administration can be parenteral, e.g., intravenous, subcutaneous, intramuscular, intracranial, intraorbital, ophthalmic, intraventricular, intracapsular, intraspinal, intracisternal, intraperitoneal, transmucosal; or administration can be oral. The compounds can be formulated in various ways, according to the route of administration.

For oral administration, the formulations can take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated or encapsulated (such as in a coating of hard gelatin or cyclodextran) using methods well known in the art (see, e.g., Baker, et al., "Controlled Release of Biological Active Agents," John Wiley and Sons, 1986).

Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (for example, sorbitol syrup, cellulose derivatives or hydrogenated edible fats); emulsifying agents (for example, lecithin may serve this function, or acacia); non-aqueous vehicles (for example, almond oil, oily esters, ethyl alcohol or fractionated vegetable oils); and preservatives (for example, methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound.

For buccal or sublingual administration the formulations can take the form of tablets or lozenges formulated in conventional manner.

The formulations can be prepared for parenteral administration by injection, for example, by bolus injection or continuous infusion. Formulations for injection can be presented in unit dosage form, for example, in ampoules or in multi-dose containers, with an added preservative. The formulations can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, for example, sterile pyrogen-free water, before use.

The formulations can also be prepared in rectal compositions such as suppositories or retention enemas, for example, containing conventional suppository bases such as cocoa butter or other glycerides.

The formulations can also be provided as a depot preparation. Such long acting formulations may be administered by implantation (for example subcutaneously or intramuscularly) or by intramuscular injection. Thus, for example, the formulations can be prepared with suitable polymeric or hydrophobic materials (for example as an emulsion in an acceptable oil) or ion exchange resins, or as sparingly soluble derivatives, for example, as a sparingly soluble salt.

Because the action of the new compounds is in the central nervous system, delivery techniques can be designed to permit or to enhance the ability of the formulation to cross the blood-brain barrier. Such techniques are known in the art (for example, see PCT WO 89/10134, Cloughesy and Black, J. Neurooncol., 26:125–132, 1995; and Begley, J. Pharm. Pharmacol., 48:136–146, 1996, all of which are incorporated herein in their entirety). Components of a formulation can also be modified (e.g., chemically) using methods known in the art to facilitate their entry into the CNS.

In some cases, it may be desirable to deliver a compound formulation directly to the nervous system, especially when one or more components of a formulation do not cross the blood-brain barrier. Examples of such methods are intraventricular injection (Kordower et al., Exp. Neurol., 124:21–30, 1993) or installation of an osmotic pump (e.g., an Alzet® pump). Another example of such a method is to surgically place an Omaya reservoir-shunt with in-line filter into the cisternal space. A compound formulation in an appropriate excipient (e.g., phosphate-buffered saline) is instilled into the shunt by injection on a prescribed basis. In all cases, consideration is given to the appropriate formulation used for specific forms of delivery.

For administration by inhalation, a formulation is delivered, for example, as an aerosol spray with the use of a suitable propellant, for example, dichlorodifluoromethane, trichlorofluoromethane, dichlorotetrafluoroethane, carbon dioxide, or other suitable gas. Other suitable methods of nasal delivery known in the art can be used, including those that facilitate delivery of a predetermined dosage.

The formulations can be presented in a pack or dispenser device, which may contain one or more unit dosage forms containing the active ingredient. The pack may, for example, comprise metal or plastic foil, such as a blister pack. The pack or dispenser device can be accompanied by instructions for administration.

The therapeutic formulations of the invention can also contain a carrier or excipient, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. Suitable pharmaceutical carriers for intravenous and other parenteral administration include, for example, sterile water, physiological saline, bacteriostatic saline (i.e., saline containing about 0.9% mg/ml benzyl alcohol), phosphate-buffered saline, Hank's solution, or Ringer's lactate.

Suitable carriers for topical administration include commercially available inert gels, liquids supplemented with albumin, methylcellulose, or a collagen matrix. Typical of such formulation are ointments, creams, and gels. Preferred carriers for topical administration are those that facilitate penetration of the skin by the new compound.

Methods for making such formulations are well known and can be found in, for example, *Remington's Pharmaceutical Sciences* (Gennaro, ed., Williams & Wilkins, Baltimore, Md.). The compounds described herein can also be administered as at least one physiologically acceptable salt such as a chloride salt, a bromide salt, or an acetate salt.

Treatment with the New Compounds

In one example of the use of the new compounds and methods, a cocaine addict is treated with one of the new drugs, given either orally or systemically. Once the half-life of the drug is determined using well-known methods, a dosing regimen (including dosage and dosing frequency) is established. In clinical trials of the drugs, tests are used to determine efficacy (defined, for example, as effectiveness in causing a person treated with the drug to stop using cocaine). Levels of cocaine in the body would also be monitored in the clinical trials.

A therapeutically effective amount of the compound is a quantity of compound that, after being administered to an individual who has, for example, an addiction to cocaine, brings about an amelioration of the disease processes and conditions associated with the addiction without causing unacceptable side effects.

The practitioner can determine the appropriate dosage for administration to a human or experimental animal patient. The amount of a compound that is administered will depend on a number of factors, including the general health, size, age, and gender of the individual, as well as the route of administration. It will also depend on the degree and severity of the individual's addiction. Typically, however, between about 100 µg and 5.0 g, e.g., 0.01 to 10 mg/kg, of the compound can be administered to the individual per day. For example, about 1 to 1000 mg (e.g., 1 to 100 mg or 1 to 30 mg) can be administered orally (e.g., in the form of a pill, tablet, syrup, suspension, or capsule) or nasally (e.g., in the form of an inhalant) each day. The compound can also be administered intravenously (e.g., by injection) into the systemic vascular compartment. Still other appropriate modes of administration include systemic administration, intramuscular, intradermal, subcutaneous, intraperitoneal, and topical administration.

Imaging with the New Compounds

Morphinans labeled, e.g., with isotopes of fluorine-18 or iodine-123, are useful for studying how brain opioid receptors change when, for example, substance abusers undergo drug withdrawal treatment programs. Positron emission tomography (PET) and single-photon emission tomography (SPECT) scans can be used for comparing changes in opioid receptor binding from baseline, through drug withdrawal, and through treatment. By comparing the timeline of these changes to changes in patient abuse patterns, researchers can predict time to relapse.

Successful visualization of receptors with PET or SPECT requires a ligand that possesses both high affinity and low nonspecific binding. Of the commonly used positron-emitting isotopes, fluorine-18 ($^{18}$F) offers considerable advantages, including a relatively long half-life (109 minutes) that permits imaging when receptor-specific binding is at its highest. Iodine-123 ($^{123}$I; half-life=13 hours) offers similar advantages for SPECT imaging. In view of their high affinity and low nonspecific binding, compounds 3 and 10, which include fluorine atoms, and compounds 34 and 35, which include iodine, are particularly well suited for use in PET and SPECT imaging, respectively. Other compounds in FIGS. 1A and 1B can also be used if properly labeled.

EXAMPLE

The following example, while not limiting the scope of the invention described in the claims, provides additional guidance for the use of the new compounds for imaging.

The new morphinans, when properly labeled, e.g., with isotopes of fluorine-18 and/or iodine-123, are useful for studying how brain opioid receptors change when, for example, substance abusers undergo drug withdrawal treatment programs. In this example, [123-I](−)-3-hydroxy-N-(E)-iodoallylmorphinan ([123-I]-MCL-118) was prepared and evaluated by measuring SPECT regional brain uptake in a baboon brain.

(−)-3-hydroxy-N-(E)-tributylstannylallylmorphinan was prepared using techniques reported in Neumeyer et al., Bioorg. Med. Chem. Lett., 71:2735 (2001), was converted to the 123-I labeled compound MCL-118 by the procedure of Baldwin et al., Nucl. Med. Biol., 20:597 (1993), a procedure used for the conversion of methyl 3-beta-4-tributylstannylphenyl)tropane-2-beta-carboxylate to [123-I]-beta-CIT.

Figure 5:
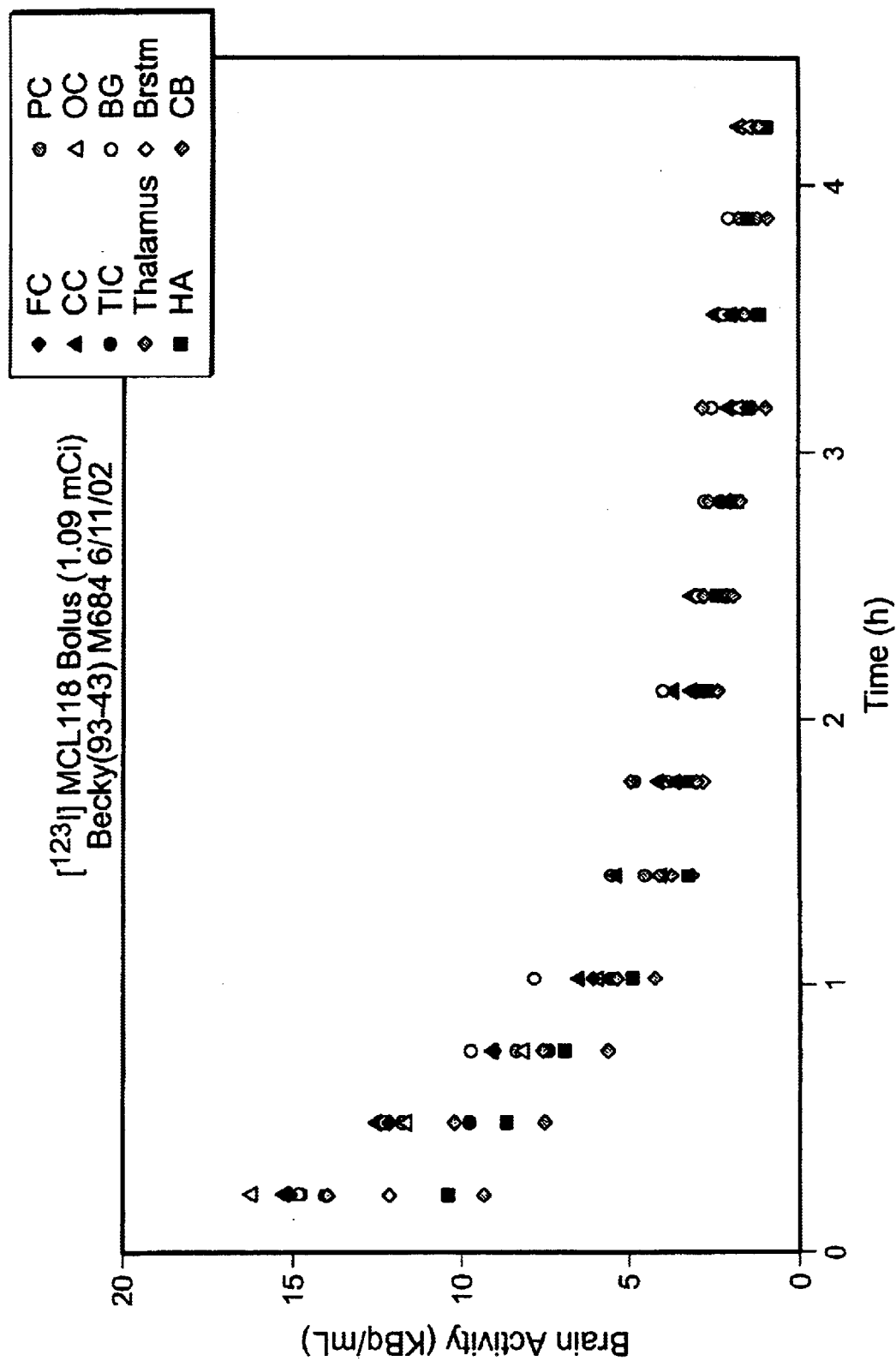
FIG. 5 is a graph that illustrates the results of administering one of the new labeled compounds to a baboon, and imaging the distribution of the compound in the brain over time using SPECT imaging.

The radiopharmaceutical was formulated in sterile isotonic saline containing about 1 mL L-ascorbic acid and 5% ethanol, pH was 6.5. 1.09 mCi of the radiopharmaceutical was administrated through an intravenous line. Data were acquired with a brain-dedicated SPECT camera performed with the AS-SPECT device (Digital Scintigraphics, Cambridge, Mass.). The brain activity (KBg/mL) and distribution over four hours is shown in the graph in FIG. 5. In the graph, FC stands for the frontal cortex, PC—Piriform Cortex, BG—Basal Ganglia, CB—Cerebellum, HA—Hypothalamus, OC—Occipital Cortex, TIC—Temporal Cortex, and CC—Cengulate Cortex, which are all areas of the brain.

The data show high uptake within 15–30 minutes in those areas of the brain (OC, thalamus, brain stem, CC, and PC) containing the highest concentration of kappa and mu receptors. In addition, the radiopharmaceutical is almost completely washed out in 4 hours from all areas of the brain.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I,

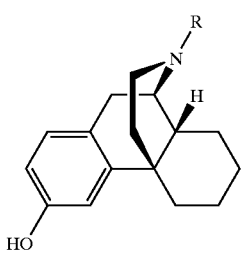

(I)

wherein R is 3-fluoropropyl (3); 2-ethoxyethyl (5); 2-methoxyethyl (6); 3,3,3-trifluoropropyl (10); 3-cyanopropyl (12); (2-furyl)methyl (22); 3-(2-thienyl)-3-oxo-propyl (26); 3-(2-furyl)-3-oxo-propyl (28); 3-(2-thienyl)-3-hydroxy-propyl (29); 3-(2-furyl)-3-hydroxy-propyl (31); 3-idoprop-(2E)-enyl (34); or 3-idoprop-(2Z)-enyl (35); 3-(tri-n-butylstannyl)-prop-(2E)-enyl (32); 3-(tri-n-butylstannyl)-prop-(2Z)-enyl (33); or a salt thereof.

2. The compound of claim 1, wherein R is 3, 5, 6, 10, 12, 26, 28, 29, 31, 34, or 35, or a salt thereof.

3. The compound of claim 2, wherein R is 3.
4. The compound of claim 2, wherein R is 5.
5. The compound of claim 2, wherein R is 6.
6. The compound of claim 2, wherein R is 10.
7. The compound of claim 2, wherein R is 12.
8. The compound of claim 2, wherein R is 34.
9. The compound of claim 1, wherein R is 35.
10. A pharmaceutical formulation comprising the compound of claim 1, and a physiologically acceptable excipient.
11. A pharmaceutical formulation comprising the compound of claim 2, and a physiologically acceptable excipient.
12. A method of single-photon computed tomography (SPECT) imaging of opioid receptors in a subject, the method comprising:

obtaining a compound of claim 1 and labeling the compound with a radioactive label, administering the labeled compound to the subject; and obtaining scans with a SPECT camera to image the opioid receptors.

13. The method of claim 12, wherein the radioactive label is $^{123}$I.
14. The method of claim 12, wherein R is 34.
15. The method of claim 12, wherein R is 35.
16. A SPECT imaging reagent comprising a $^{123}$I-labeled compound of Formula I,

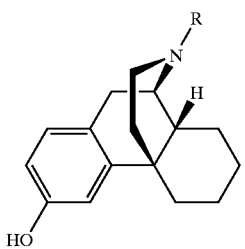

(I)

wherein R is $^{123}$I-labeled 3-iodoprop-(2E)-enyl (34) or 3-idoprop-(2Z)-enyl (35).

17. A method of positron emission tomography (PET) imaging of brain opioid receptors in a subject, the method comprising:

obtaining a compound of claim 1 and labeling the compound with a radioactive label;

administering the labeled compound to the subject; and obtaining brain scans with a PET camera to image the opioid receptors.

18. The method of claim 17, wherein the radioactive label is $^{18}$F.
19. The method of claim 17, wherein R is 3.
20. The method of claim 17, wherein R is 10.
21. A PET imaging reagent comprising an $^{18}$F-labeled compound of Formula I,

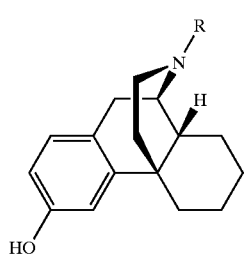

(I)

wherein R is $^{18}$F-labeled 3-fluoropropyl (3) or 3,3,3-trifluoropropyl (10).

22. A method of treating a patient addicted to cocaine, the method comprising administering to the patient an effective amount of a compound of claim 1 or one or more compounds of Formula I,

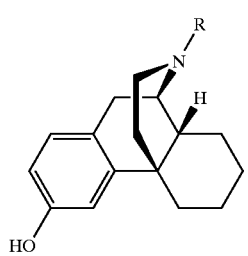

(I)

wherein R is 2-methylpropyl (4); 2-propenyl (8); 2-propynyl (9); 2-cyanoethyl (11).

23. The method of claim 22, wherein R is 3, 5, 6, 10, 12, 26, 28, 29, 31, 34, or 35.
24. The method of claim 22, wherein R is 4, 8, 9, or 11.
25. The method of claim 22, wherein R is 3, 9, or 34.

* * * * *